US008409908B2

(12) United States Patent
Li et al.

(10) Patent No.: US 8,409,908 B2

(45) Date of Patent: Apr. 2, 2013

(54) APPARATUS FOR REDUCING PHOTODIODE THERMAL GAIN COEFFICIENT AND METHOD OF MAKING SAME

(75) Inventors: Wen Li, Clifton Park, NY (US); Jonathan D. Short, Saratoga Springs, NY (US); George E. Possin, Niskayuna, NY (US)

(73) Assignee: General Electric Company, Niskayuna, NY (US)

(*) Notice: Subject to any disclaimer, the term of this patent is extended or adjusted under 35 U.S.C. 154(b) by 634 days.

(21) Appl. No.: 12/512,714

(22) Filed: Jul. 30, 2009

(65) Prior Publication Data

US 2011/0024711 A1 Feb. 3, 2011

(51) Int. Cl.
*H01L 21/00* (2006.01)

(52) U.S. Cl. .................. 438/73; 257/443; 257/E27.133

(58) Field of Classification Search .................. 257/443, 257/E27.133; 438/73

See application file for complete search history.

(56) References Cited

U.S. PATENT DOCUMENTS 4,686,554 A * 8/1987 Ohmi et al. .................. 257/443
5,583,352 A * 12/1996 McIntyre et al. ............ 257/186
6,426,991 B1 7/2002 Mattson et al.
6,707,046 B2 3/2004 Possin et al.
6,762,473 B1 7/2004 Goushcha et al.
6,933,489 B2 8/2005 Fujii et al.
2007/0252240 A1* 11/2007 Andresen et al. ............ 257/607

OTHER PUBLICATIONS

Goushcha et al., "Silicon PIN Photodiode Array for Medical Imaging Applications: Structure, Optical Properties and Temperature Coefficients," IEEE 2005 Nuclear Science Symposium and Medical Imaging Conference.

* cited by examiner

*Primary Examiner* — Steven J Fulk

(74) *Attorney, Agent, or Firm* — Marie-Claire G. Maple

(57) ABSTRACT

An apparatus for reducing photodiode thermal gain coefficient includes a bulk semiconductor material having a light-illumination side. The bulk semiconductor material includes a minority charge carrier diffusion length property configured to substantially match a predetermined hole diffusion length value and a thickness configured to substantially match a predetermined photodiode layer thickness. The apparatus also includes a dead layer coupled to the light-illumination side of the bulk semiconductor material, the dead layer having a thickness configured to substantially match a predetermined thickness value and wherein an absolute value of a thermal coefficient of gain due to the minority carrier diffusion length property of the bulk semiconductor material is configured to substantially match an absolute value of a thermal coefficient of gain due to the thickness of the dead layer.

4 Claims, 7 Drawing Sheets

APPARATUS FOR REDUCING PHOTODIODE THERMAL GAIN COEFFICIENT AND METHOD OF MAKING SAME

BACKGROUND OF THE INVENTION

The invention relates generally to diagnostic imaging and, more particularly, to an apparatus for reducing photodiode thermal gain coefficient in a photodiode array.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

A CT detector typically has stringent specifications on the channel-to-channel or pixel-to-pixel differential signal error, especially for the center part of the detector ring. For example, the tolerance for pixel-to-pixel differential signal error may be as low as 200 ppm. One of the typical contributions to the differential signal error of the detector is from the photodiode arrays due to the existence of a diode thermal coefficient of gain ("gain tempco") and due to temperature variations within and between diode arrays. To minimize this contribution, CT detectors are designed with low temperature variation at the diode arrays. With the increase of the detector size to provide more and more coverage, this thermal design becomes more and more challenging. Other methods for minimizing contributions due to temperature variations include thermal management/cooling systems designed to remove excess temperature from the CT detectors. These thermal management systems, however, are often bulky and add excess weight and complexity to the CT gantry system.

Therefore, it would be desirable to design an apparatus capable of low differential signal errors due to temperature variations within a photodiode array of any size.

BRIEF DESCRIPTION OF THE INVENTION

In accordance with one aspect of the invention, an apparatus includes a bulk semiconductor material having a light-illumination side. The bulk semiconductor material includes a minority charge carrier diffusion length property configured to substantially match a predetermined hole diffusion length value and a thickness configured to substantially match a predetermined photodiode layer thickness. The apparatus also includes a dead layer coupled to the light-illumination side of the bulk semiconductor material, the dead layer having a thickness configured to substantially match a predetermined thickness value and wherein an absolute value of a thermal coefficient of gain due to the minority carrier diffusion length property of the bulk semiconductor material is configured to substantially match an absolute value of a thermal coefficient of gain due to the thickness of the dead layer.

In accordance with another aspect of the invention, a method includes selecting a photodiode bulk material having a minority carrier diffusion length configured to substantially match a predetermined minority carrier diffusion length value and removing a portion of the selected photodiode bulk material to form a photodiode layer having a thickness configured to substantially match a predetermined photodiode layer thickness. The method also includes forming a dead layer on a light-illumination surface of the photodiode layer such that a thickness of the dead layer is configured to substantially match a predetermined dead layer thickness and such that a thermal coefficient of gain due to the thickness of the dead layer is configured to substantially nullify a thermal coefficient of gain due to the minority carrier diffusion length of the photodiode bulk material.

In accordance with another aspect of the invention, a method of manufacturing a back-illuminated photodiode includes calculating a desired minority carrier diffusion length, a desired photodiode wafer thickness, and a desired dead layer thickness such that a thermal coefficient of gain due to the desired dead layer thickness substantially cancels a thermal coefficient of gain due to the desired minority carrier diffusion length. The method also includes providing a photodiode bulk material having a minority carrier diffusion length configured to substantially match the desired minority carrier diffusion length value and thinning the selected photodiode bulk material to form a photodiode layer having a thickness configured to substantially match the desired photodiode wafer thickness. The method further includes doping a dead layer on a light-illumination surface of the photodiode layer such that a thickness of the dead layer substantially matches the desired dead layer thickness.

Various other features and advantages will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION

The operating environment of the invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
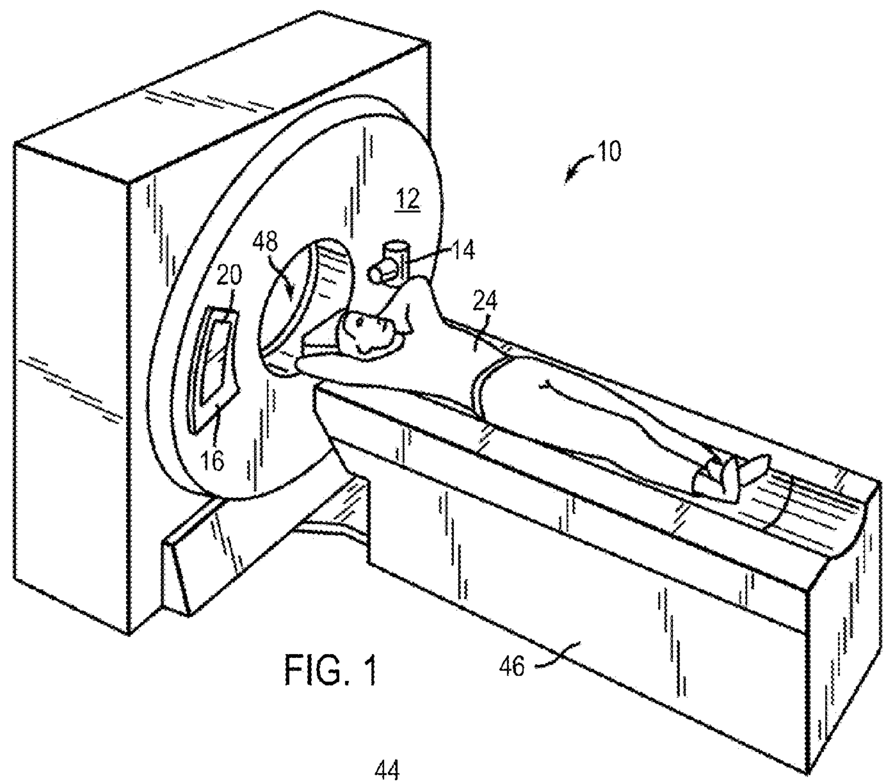
FIG. 1 is a pictorial view of a CT imaging system.
Figure 2:
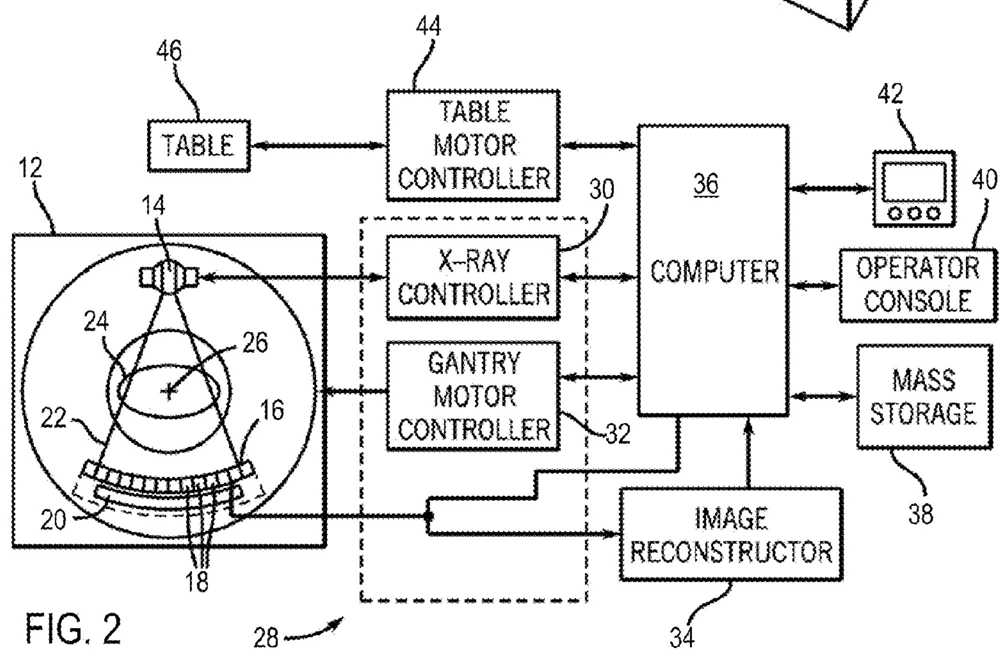
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays toward a detector assembly or collimator 16 on the opposite side of the gantry 12. Referring now to FIG. 2, detector assembly 16 is formed by a plurality of detectors 18 and a data acquisition system (DAS) 20. The plurality of detectors 18 sense the projected x-rays 22 that pass through a medical patient 24, and DAS 20 converts the data to digital signals for subsequent processing. Each detector 18 produces an analog electrical signal that represents the intensity of an impinging x-ray beam and hence the attenuated beam as it passes through the patient 24. During a scan to acquire x-ray projection data, gantry 12 and the components mounted thereon rotate about a center of rotation 26.

Rotation of gantry 12 and the operation of x-ray source 14 are governed by a control mechanism 28 of CT system 10. Control mechanism 28 includes an x-ray controller 30 that provides power and timing signals to an x-ray source 14 and a gantry motor controller 32 that controls the rotational speed and position of gantry 12. An image reconstructor 34 receives sampled and digitized x-ray data from DAS 20 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 20, x-ray controller 30 and gantry motor controller 32. In addition, computer 36 operates a table motor controller 44 which controls a motorized table 46 to position patient 24 and gantry 12. Particularly, table 46 moves patients 24 through a gantry opening 48 of FIG. 1 in whole or in part.

Figure 3:
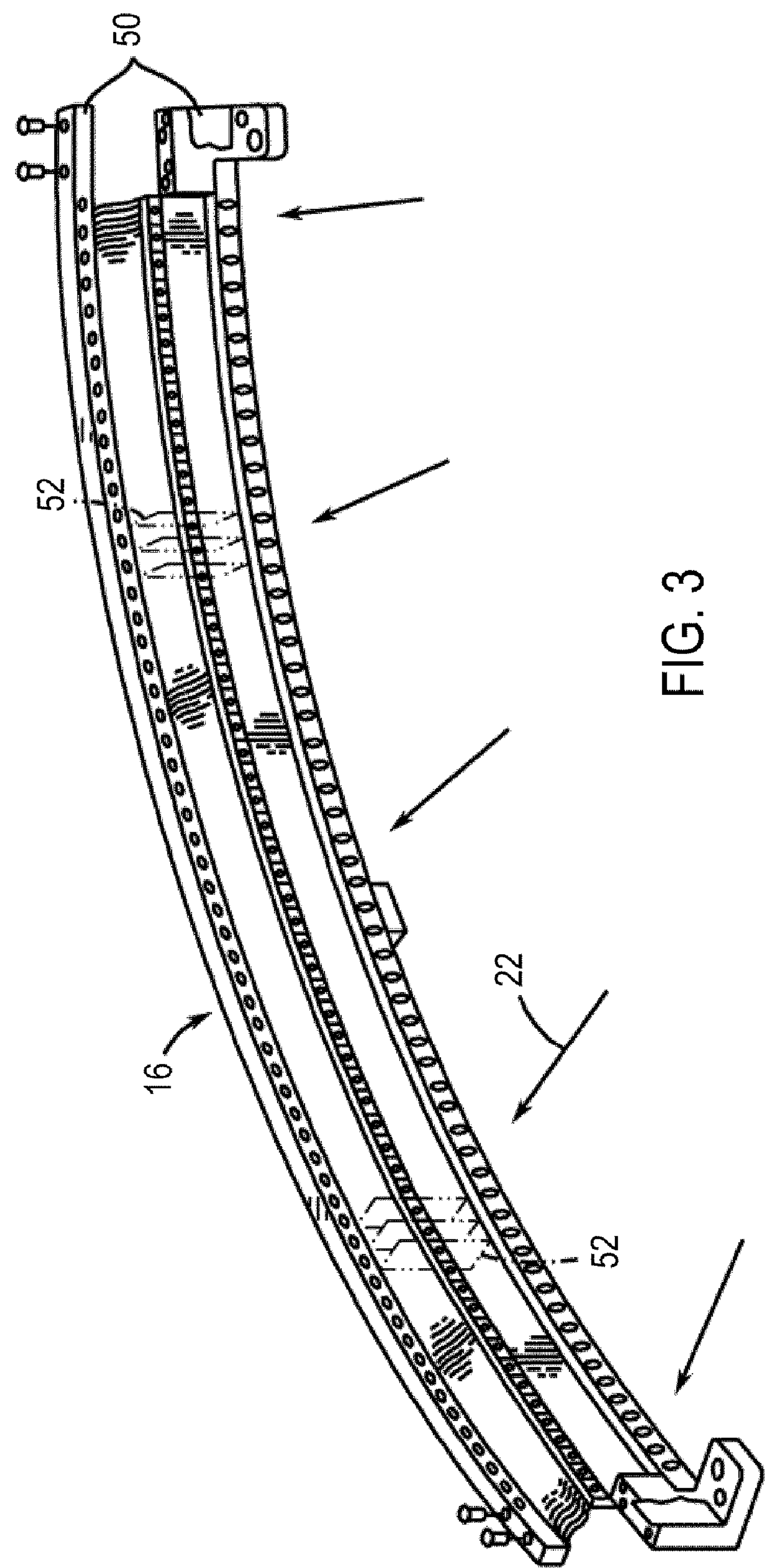
FIG. 3 is a perspective view of one embodiment of a CT system detector array.
Figure 4:
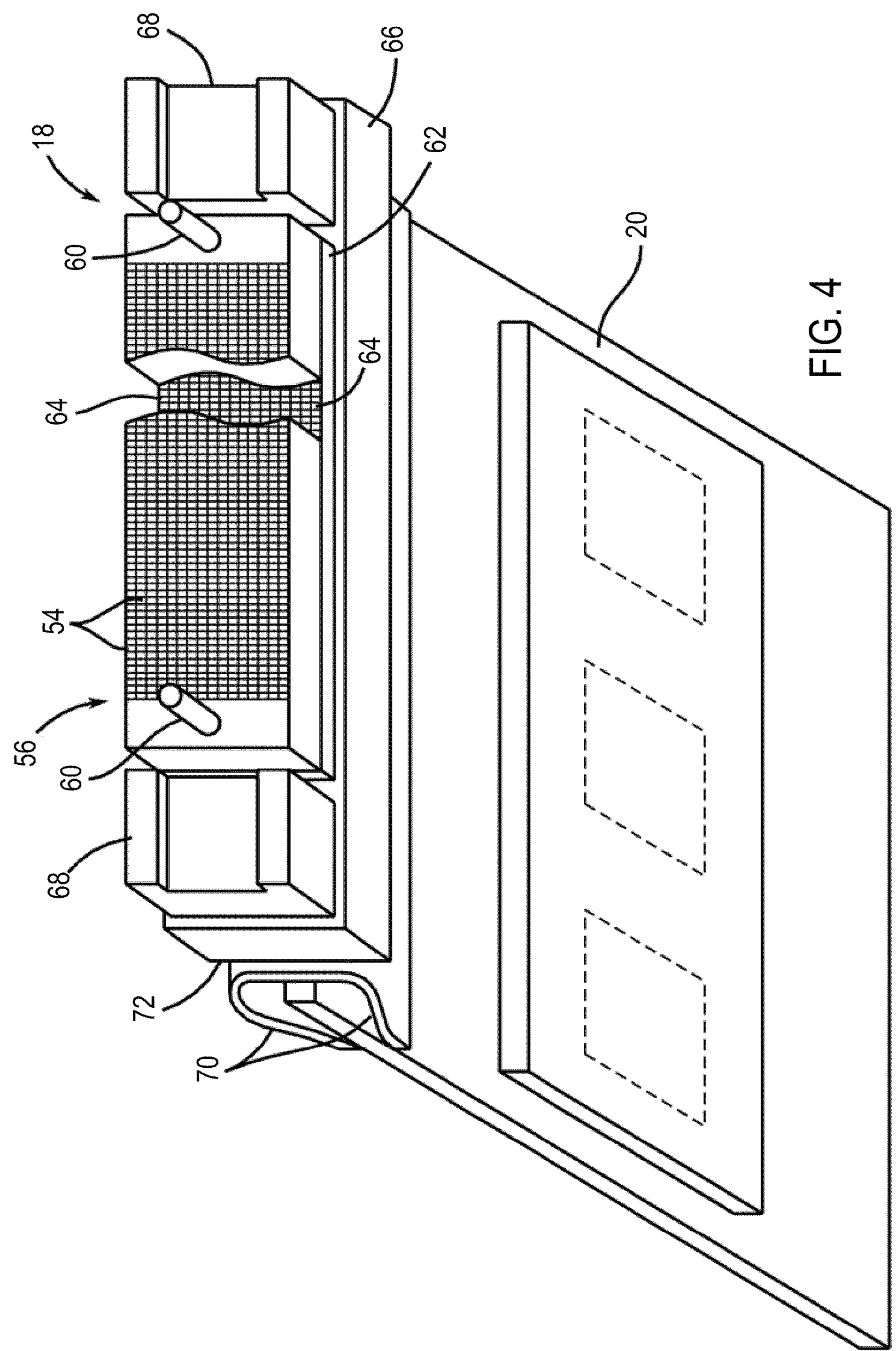
FIG. 4 is a perspective view of one embodiment of a detector.

As shown in FIGS. 3 and 4, detector assembly 16 includes a pair of rails 50 having a plurality of collimating blades or plates 52 placed therebetween. Plates 52 are positioned to collimate x-rays 22 before such beams impinge upon, for instance, detector 18 positioned on detector assembly 16. In one embodiment, detector assembly 16 includes fifty-seven detectors 18, each detector 18 including a number of detector elements 54 arranged in a pack 56 and having an array size of 64×16 of pixel elements 54. As a result, detector assembly 16 has sixty-four rows and nine-hundred twelve columns (16×57 detectors) which allows sixty-four simultaneous slices of data to be collected with each rotation of gantry 12.

Detector 18 includes DAS 20 and a pair of pins 60 positioned within pack 56 relative to detector elements 54. Pack 56 is positioned on a backlit diode array 62 having a plurality of diodes 64. Backlit diode array 62 is in turn positioned on a multi-layer substrate 66. A pair of spacers 68 are positioned on multi-layer substrate 66. Detector elements 54 are optically coupled to backlit diode array 62, and backlit diode array 62 is in turn electrically coupled to multi-layer substrate 66. A plurality of flex circuits 70 are attached to a face 72 of multi-layer substrate 66 and to DAS 20. Detectors 18 are positioned within detector assembly 16 by use of pins 60.

In the operation of one embodiment, x-rays impinging within detector elements 54 generate optical photons which traverse pack 56, thereby generating an analog electrical charge signal at a diode within backlit diode array 62. The analog signal generated is carried through multi-layer substrate 66, through flex circuits 70, to DAS 20 wherein the analog signal is converted to a digital signal.

Figure 5:
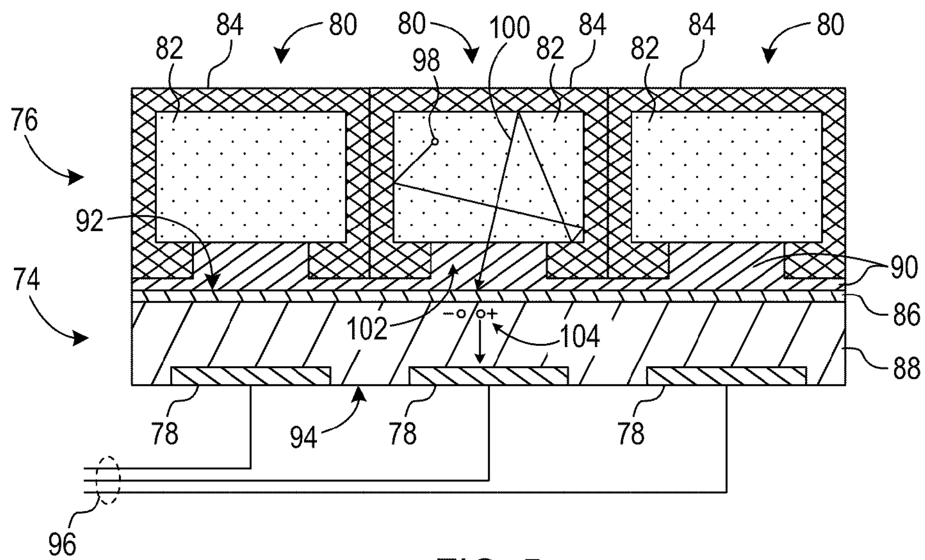
FIG. 5 is a cross-sectional view of a photodiode array and scintillator pack according to one embodiment of the invention.

FIG. 5 shows a cross-sectional view of a photodiode array 74 and a scintillator pack 76 according to one embodiment of the invention. Array 74 and pack 76 illustrated embodiments of a plurality of photodiodes 78 and scintillator detector elements 80 that may be used in CT imaging system 10 and, in particular, in backlit diode array 62 and detector pack 56 of detector 18 illustrated in FIG. 4. Each scintillator element 80 includes a scintillator material 82 having a light reflecting coating 84 attached thereto. Photodiode array 74 includes a dead layer 86, a bulk photodiode material 88 such as silicon, and photodiodes 78. Photodiode array 74 is coupled to scintillator pack 76 via a transparent optical coupler 90.

Photodiode array 74 is a back-illuminated photodiode array. A back or light-illumination side 92 of array 74 adjacent to dead layer 86 is opposite a front side 94 of array 74 adjacent to the photodiode junction 78. Output connections 96 from photodiodes 78 extended from the photodiodes 78 and from the front side 94 of photodiode array 74. When an x-ray 98 impinges upon scintillator material 82, a light signal 100 is generated therefrom that is reflected via light reflecting coating 84 through an opening 102 in coating 84 and through transparent optical coupler 90 toward the back side 92 of photodiode array 74. A free charge carrier 104 generated in photodiode array 74 in response to the light signal 100 travels toward the front side 94 of photodiode array 74, and a signal is generated when the free charge carrier 104 is collected at the diode junction 78.

Photodiode gain tempco and other factors such as temperature variations within and between photodiodes within photodiode arrays may lead to differential signal errors. Contributions to the gain tempco of back-illuminated photodiodes include a geometry term and a recombination term. The gain tempco may be determined via the following equation:

$$\text{Gain Tempco}(ND, Wn, W\_Si, \lambda, Lp) = Gg(Wn, \lambda) + Gr(ND, W\_Si, \lambda, Lp) \quad \text{(Eqn. 1)},$$

where ND is the wafer intrinsic doping density, W_Si is the wafer thickness, Wn is the backside N+ doping depth, $\lambda$ is the wavelength of light from the scintillator material, and Lp is the hole diffusion length.

Figure 6:
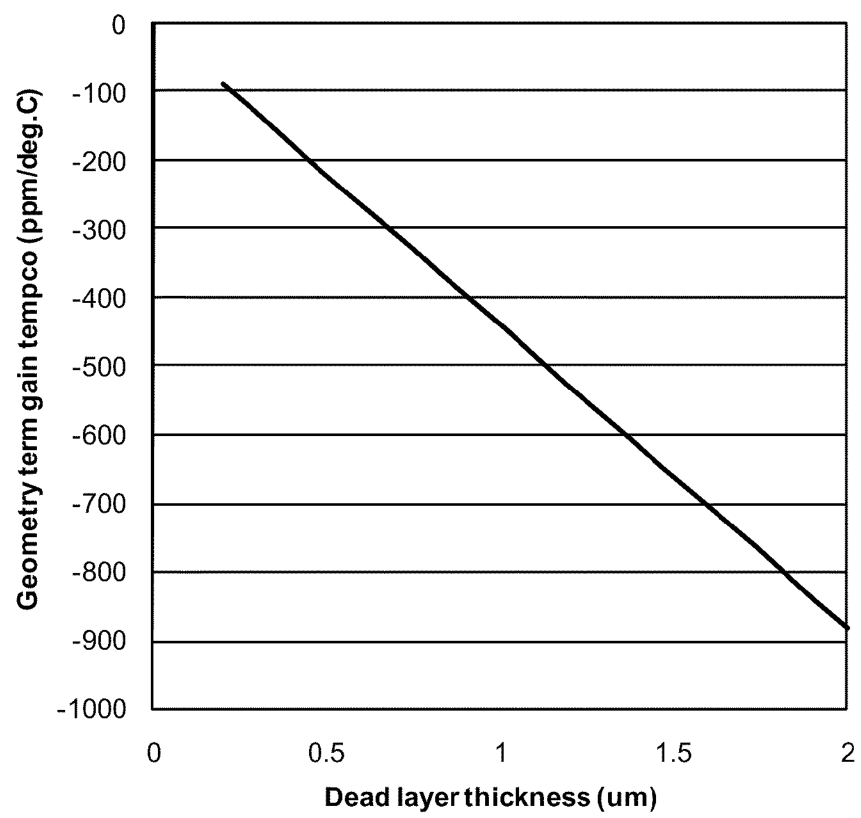
FIG. 6 is a graph showing a relationship between gain tempco and dead layer thickness of a photodiode array according to an embodiment of the invention.

The geometry term, Gg(Wn, $\lambda$), is determined by the thickness of the dead layer at the light illumination side, and it is always negative. FIG. 6 illustrates a graph showing a relationship between gain tempco and dead layer thickness of a photodiode array due to the geometry term according to an embodiment of the invention. The geometry term captures the tempco of signal loss due to the N+ dead layer. It is determined by the tempco of the light absorption coefficient, ($d\alpha$)/(dT). The geometry term may be determined via the following equation:

$$G_g(W_n, \lambda) = \left(\frac{d\eta}{d\alpha}\right)\cdot\left(\frac{d\alpha}{dT}\right)\Big/\eta, \quad \text{(Eqn. 2)}$$

where $\alpha$ is the absorption coefficient, T is the temperature coefficient, and $\eta$ is the quantum efficiency QE(Wn, W_Si, Lp, $\alpha$).

Figure 7:
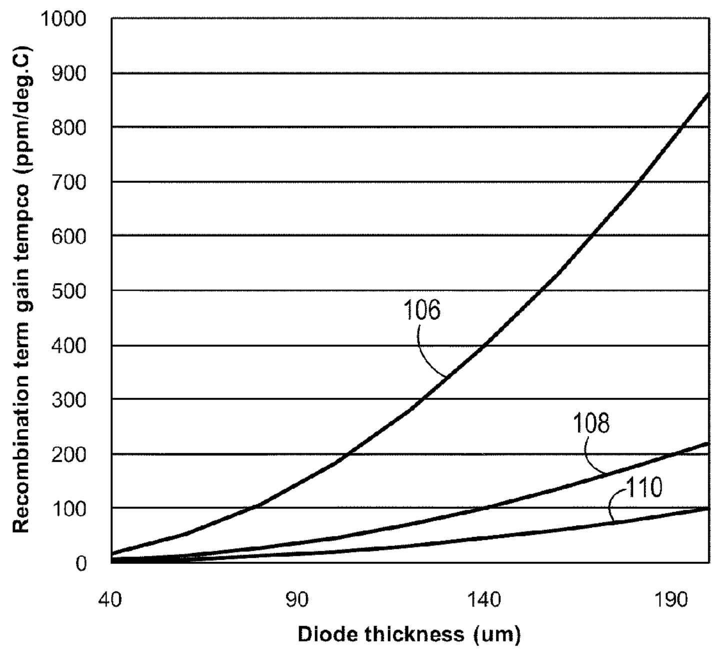
FIG. 7 is a graph showing a relationship between gain tempco, diode layer thickness, and hole diffusion length of a photodiode array according to an embodiment of the invention.

The recombination term, Gr(ND, W_Si, $\lambda$, Lp), exists due to the temperature-dependent recombination of electrons and holes when the minority charge carriers diffuse across the diode thickness before getting collected by the photodiodes. The recombination term captures the tempco of signal loss due to electron/hole recombination. The recombination term is always positive and is determined by the hole diffusion length or lifetime of minority charge carriers and the diode thickness. FIG. 7 illustrates a graph showing a relationship between gain tempco, diode layer thickness, and hole diffusion length of a photodiode array due to the recombination term according to an embodiment of the invention. A graph lines 106, 108, and 110 illustrate the relationship between the recombination term gain tempco and diode layer thickness for a photodiode bulk material having a hole diffusion length of 1 mm, 2 mm, and 3 mm, respectively. The recombination term may be determined via the following equation:

$$\begin{aligned} G_r(ND, \text{W\_Si}, \lambda, Lp) &= \left(\frac{d\eta}{dLp}\right)\cdot\left(\frac{dLp}{dT}\right)\Big/\eta \quad \text{(Eqn. 3),} \\ &= \left(\frac{d\eta}{dLp}\right)\cdot\left[\frac{Lp}{2}\cdot\frac{1}{\tau}\cdot\left(\frac{d\tau}{dT}\right)\right]\Big/\eta \end{aligned}$$

$$\text{where } \tau = \frac{Lp^2}{Dp}.$$

With properly selected diode parameters (dead layer and diode thickness, and diffusion length of minority charge carriers), the geometry and recombination terms of gain tempco can be designed to cancel each other. This yields a CT photodiode array with zero or near-zero gain tempco, which will provide relief to any temperature control requirements for the CT diode array. In one example, the temperature control requirement may be set to a limit to accommodate +/−200 ppm/° C. gain tempco of conventional CT photodiode arrays. As will be described below with respect to FIG. 8, embodiments of the invention allow for the design and manufacture of a CT photodiode array meeting or exceeding a gain tempco requirement of +/−30 ppm/° C. For example, it is possible to manufacture a CT photodiode array according to embodiments of the invention such that the gain tempco is within the range of +/−20 ppm/° C. Accordingly, the gain tempco contributions due to the geometry term substantially cancel or nullify the gain tempco contributions due to the recombination term. As used herein, a zero or near-zero gain tempco comprises a range within +/−30 ppm/° C. such that an absolute value of the gain tempco contributions due to the geometry term is no more than 30 ppm/° C. of the absolute value of the gain tempco contributions due to recombination term.

Figure 8:
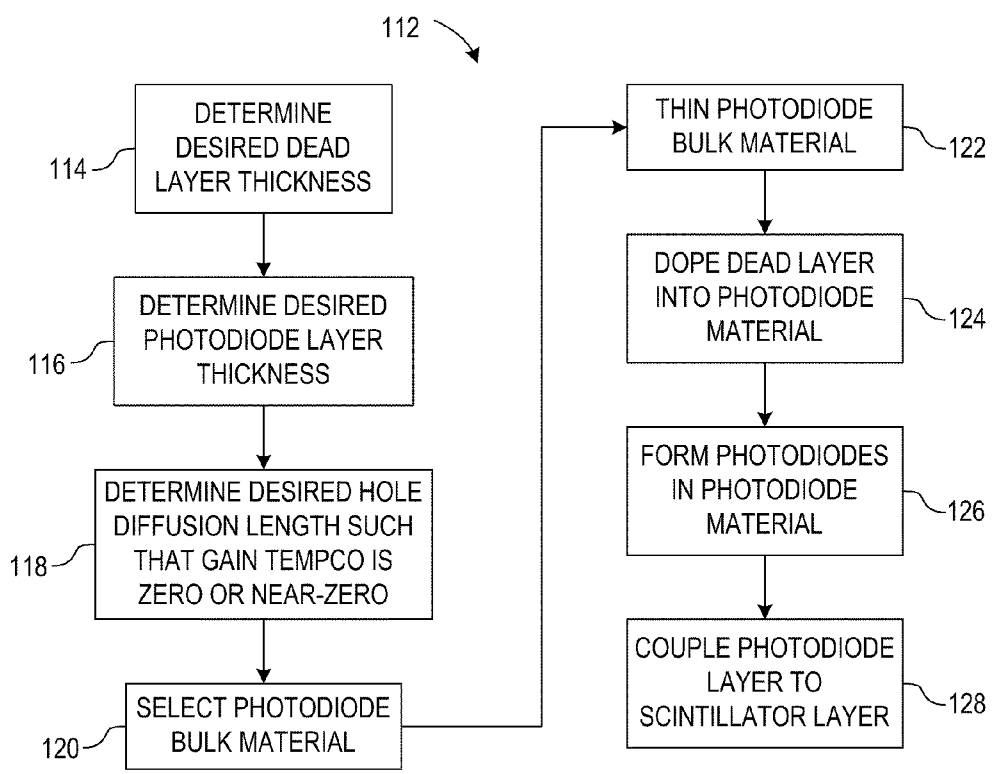
FIG. 8 is a flow chart illustrating a technique for manufacturing a photodiode array according to an embodiment of the invention.

FIG. 8 is a flow chart illustrating a technique 112 for manufacturing a back-illuminated photodiode array such as photodiode array 74 of FIG. 5 according to an embodiment of the invention. Technique 112 includes determining a desired dead layer thickness for the photodiode layer at block 114. The desired dead layer thickness may be determined, for example, based on a desired quantum efficiency for the diode. At block 116, a desired photodiode layer thickness is determined. The desired photodiode layer thickness may be determined based on a cross-talk threshold. For example, the desired photodiode layer thickness may be set to 100 μm such that the amount of cross-talk occurring in the photodiode layer falls below a certain value. At block 118, the desired hole diffusion length that results in a gain tempco of zero or near-zero based on the gain tempco contributions due to the geometry and recombination terms may be determined based on the desired dead layer thickness value, the desired photodiode layer thickness value, and Eqns. 1-3.

Given the determined desired hole diffusion length value, photodiode wafers of photodiode bulk material having a hole diffusion length value matching the desired hole diffusion length value are selected at block 120. According to an embodiment of the invention, the photodiode wafers may be manufactured to have the specific hole diffusion length value desired. At block 122, the photodiode bulk material is thinned to the desired photodiode layer thickness if needed. Next, an N+ dead layer is doped into one surface of the photodiode material at block 124. The dead layer is doped into the back or light-illumination side of the photodiode layer. At block 126, P+ photodiodes are formed into the front side of the photodiode layer. A detector assembly is formed at block 128 by coupling the photodiode layer to a scintillator layer or pack via a transparent optical coupler.

Figure 9:
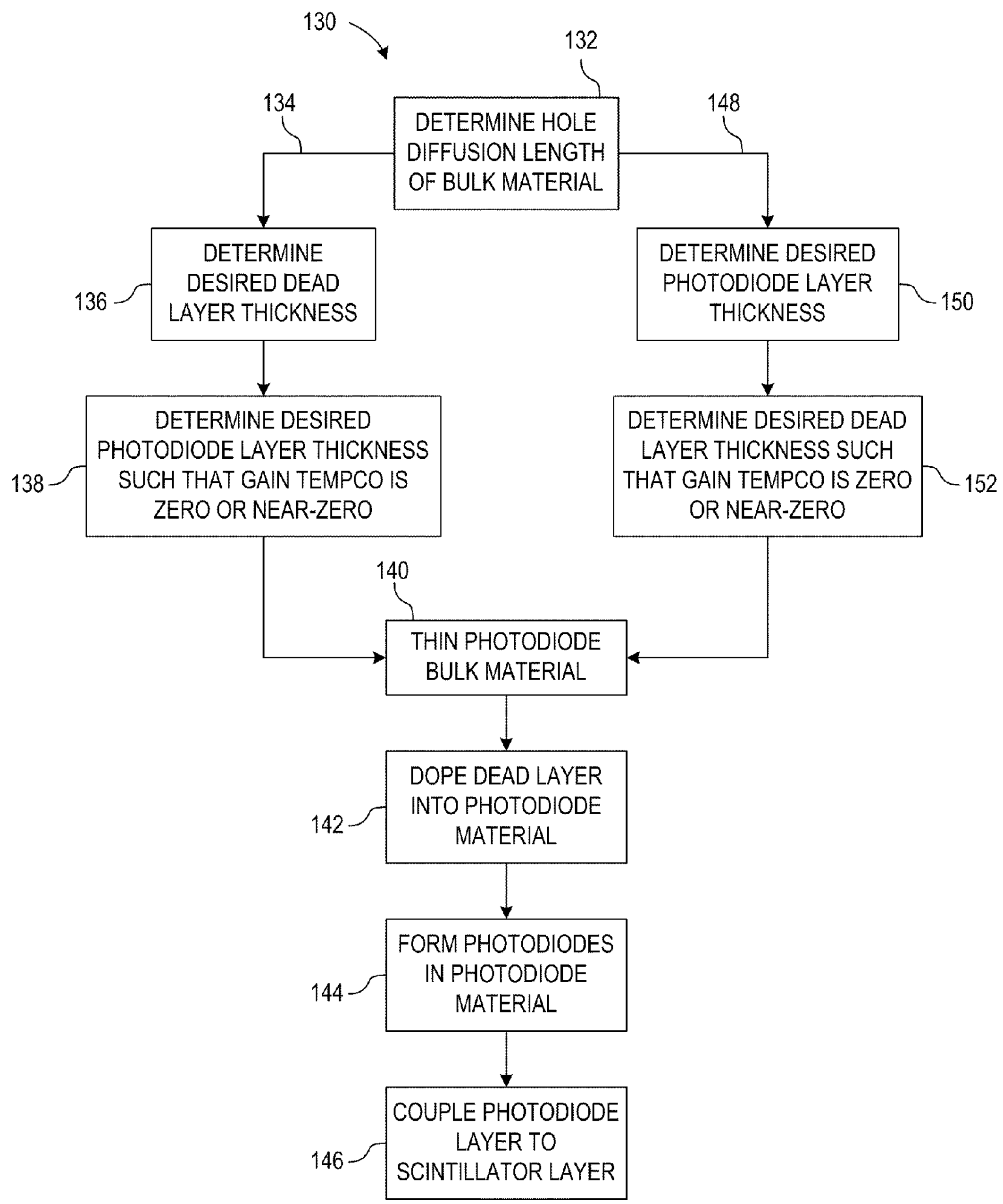
FIG. 9 is a flow chart illustrating a technique for manufacturing a photodiode array according to another embodiment of the invention.

Technique 112, as described above, determines the unknown hole diffusion length variable after first determining or setting the unknown variables of dead layer thickness and photodiode layer thickness. However, embodiments of the invention contemplate determining any two of the unknown variables prior to determining the remaining unknown variable. For example, according to an embodiment of the invention, FIG. 9 is a flow chart illustrating a technique 130 for manufacturing a back-illuminated photodiode array such as photodiode array 74 of FIG. 5 according to another embodiment of the invention. Technique 130 begins by determining the hole diffusion length of a photodiode bulk material at block 132. The photodiode bulk material may be material that is on-hand or may be manufactured to have the determined hole diffusion length.

In one embodiment 134, the desired dead layer thickness may be determined at block 136 based on, for example, a desired quantum efficiency for the dead layer. Then, the unknown desired photodiode layer thickness may be determined at block 138 that results in a gain tempco of zero or near-zero based on the gain tempco contributions due to the geometry and recombination terms based on the hole diffusion length of the photodiode bulk material, the desired dead layer thickness value, and Eqns. 1-3.

At block 140, the photodiode bulk material is thinned to the desired photodiode layer thickness if needed. Next, an N+ dead layer is doped into one surface of the photodiode material at block 142. The dead layer is doped into the back or light-illumination side of the photodiode layer. At block 144, P+ photodiodes are formed into the front side of the photodiode layer. A detector assembly is formed at block 146 by coupling the photodiode layer to a scintillator layer or pack via a transparent optical coupler.

In another embodiment 148, the desired photodiode layer thickness may be determined at block 150 based on, for example, a desired cross-talk threshold. Then, the unknown desired dead layer thickness may be determined at block 152 that results in a gain tempco of zero or near-zero based on the gain tempco contributions due to the geometry and recombination terms based on the hole diffusion length of the photodiode bulk material, the desired photodiode layer thickness value, and Eqns. 1-3. Technique 130 then continues with blocks 140-146 as described above.

Figure 10:
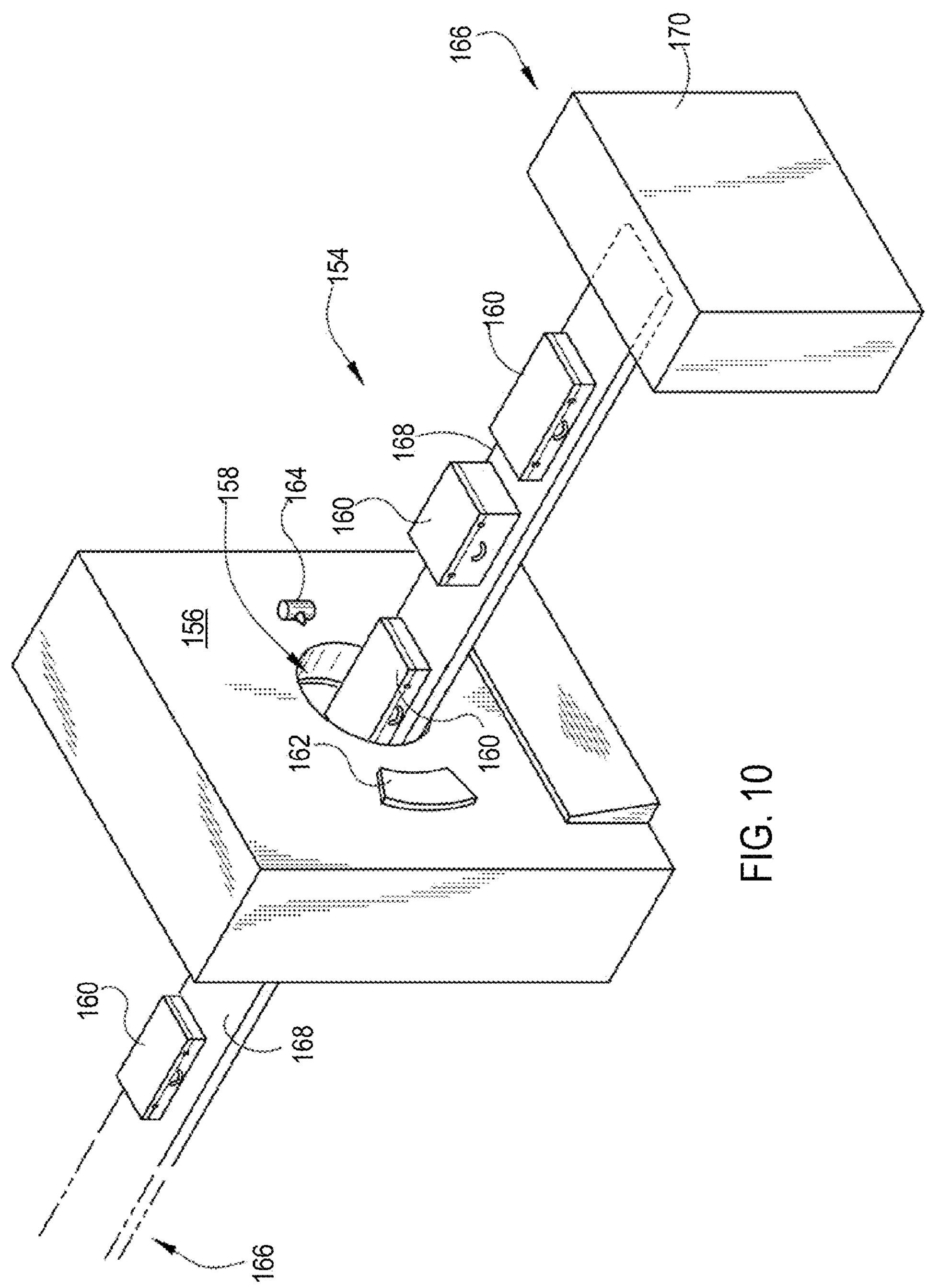
FIG. 10 is a pictorial view of a CT system for use with a non-invasive package inspection system.

FIG. 10 is a pictorial view of an x-ray imaging system 154 for use with a non-invasive package inspection system. The x-ray system 154 includes a gantry 156 having an opening 158 therein through which a plurality of packages or pieces of baggage 160 may pass. The gantry 156 houses a detector assembly 162 and a high frequency electromagnetic energy source, such as an x-ray tube 164. A conveyor system 166 is also provided and includes a conveyor belt 168 supported by a structure 170 to automatically and continuously pass packages or baggage pieces 160 through opening 158 to be scanned. Objects 160 are fed through opening 158 by conveyor belt 168, imaging data is then acquired, and the conveyor belt 168 removes the packages 160 from opening 158 in a controlled and continuous manner. As a result, postal inspectors, baggage handlers, and other security personnel may non-invasively inspect the contents of packages 160 for explosives, knives, guns, contraband, etc. One skilled in the art will recognize that gantry 156 may be stationary or rotatable. In the case of a rotatable gantry 156, system 154 may be configured to operate as a CT system for baggage scanning or other industrial or medical applications.

In accordance with one embodiment of the invention, an apparatus includes a bulk semiconductor material having a light-illumination side. The bulk semiconductor material includes a minority charge carrier diffusion length property configured to substantially match a predetermined hole diffusion length value and a thickness configured to substantially match a predetermined photodiode layer thickness. The apparatus also includes a dead layer coupled to the light-illumination side of the bulk semiconductor material, the dead layer having a thickness configured to substantially match a predetermined thickness value and wherein an absolute value of a thermal coefficient of gain due to the minority carrier diffusion length property of the bulk semiconductor material is configured to substantially match an absolute value of a thermal coefficient of gain due to the thickness of the dead layer.

In accordance with another embodiment of the invention, a method includes selecting a photodiode bulk material having a minority carrier diffusion length configured to substantially match a predetermined minority carrier diffusion length value and removing a portion of the selected photodiode bulk material to form a photodiode layer having a thickness configured to substantially match a predetermined photodiode layer thickness. The method also includes forming a dead layer on a light-illumination surface of the photodiode layer such that a thickness of the dead layer is configured to substantially match a predetermined dead layer thickness and such that a thermal coefficient of gain due to the thickness of the dead layer is configured to substantially nullify a thermal coefficient of gain due to the minority carrier diffusion length of the photodiode bulk material.

In accordance with another embodiment of the invention, a method of manufacturing a back-illuminated photodiode includes calculating a desired minority carrier diffusion length, a desired photodiode wafer thickness, and a desired dead layer thickness such that a thermal coefficient of gain due to the desired dead layer thickness substantially cancels a thermal coefficient of gain due to the desired minority carrier diffusion length. The method also includes providing a photodiode bulk material having a minority carrier diffusion length configured to substantially match the desired minority carrier diffusion length value and thinning the selected photodiode bulk material to form a photodiode layer having a thickness configured to substantially match the desired photodiode wafer thickness. The method further includes doping a dead layer on a light-illumination surface of the photodiode layer such that a thickness of the dead layer substantially matches the desired dead layer thickness.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of manufacturing a back-illuminated photodiode comprising:

calculating a desired minority carrier diffusion length, a desired photodiode wafer thickness, and a desired dead layer thickness such that a thermal coefficient of gain due to the desired dead layer thickness substantially cancels a thermal coefficient of gain due to the desired minority carrier diffusion length;

providing a photodiode bulk material having a minority carrier diffusion length configured to substantially match the desired minority carrier diffusion length value;

thinning the selected photodiode bulk material to form a photodiode layer having a thickness configured to substantially match the desired photodiode wafer thickness;

doping a dead layer on a light-illumination surface of the photodiode layer such that a thickness of the dead layer substantially matches the desired dead layer thickness.

2. The method of claim 1 wherein calculating comprises calculating the desired minority carrier diffusion length, the desired photodiode wafer thickness, and the desired dead layer thickness such that a difference between the thermal coefficient of gain due to the desired dead layer thickness and the thermal coefficient of gain due to the desired minority carrier diffusion length is no more than +/−30 ppm/° C.

3. The method of claim 1 wherein calculating comprises calculating the desired minority carrier diffusion length, the desired photodiode wafer thickness, and the desired dead layer thickness such that a difference between the thermal coefficient of gain due to the desired dead layer thickness and the thermal coefficient of gain due to the desired minority carrier diffusion length is no more than +/−20 ppm/° C.

4. The method of claim 1 further comprising forming a plurality of photodiodes in the photodiode layer on a second surface of the photodiode layer opposite the light-illumination surface.

* * * * *